United States Patent
Yamada et al.

(10) Patent No.: US 12,111,299 B2
(45) Date of Patent: Oct. 8, 2024

(54) MEASUREMENT INSTRUMENT AND METHOD FOR MEASURING TARGET SUBSTANCE USING SAME

(71) Applicant: KANAGAWA INSTITUTE OF INDUSTRIAL SCIENCE AND TECHNOLOGY, Ebina (JP)

(72) Inventors: Tetsuya Yamada, Ebina (JP); Toshihisa Osaki, Ebina (JP); Hisatoshi Mimura, Ebina (JP); Hirotaka Sugiura, Ebina (JP); Shoji Takeuchi, Tokyo (JP)

(73) Assignee: KANAGAWA INSTITUTE OF INDUSTRIAL SCIENCE AND TECHNOLOGY, Ebina (JP)

( * ) Notice: Subject to any disclaimer, the term of this patent is extended or adjusted under 35 U.S.C. 154(b) by 289 days.

(21) Appl. No.: 17/764,680

(22) PCT Filed: Oct. 2, 2020

(86) PCT No.: PCT/JP2020/037647
§ 371 (c)(1),
(2) Date: Mar. 29, 2022

(87) PCT Pub. No.: WO2021/066179
PCT Pub. Date: Apr. 8, 2021

(65) Prior Publication Data
US 2022/0326204 A1    Oct. 13, 2022

(30) Foreign Application Priority Data
Oct. 4, 2019  (JP) ................. 2019-183996

(51) Int. Cl.
*G01N 33/00*   (2006.01)
*G01N 1/38*   (2006.01)
*G01N 33/487*   (2006.01)

(52) U.S. Cl.
CPC .......... *G01N 33/0027* (2013.01); *G01N 1/38* (2013.01); *G01N 33/0047* (2013.01); *G01N 33/48721* (2013.01)

(58) Field of Classification Search
CPC .............. G01N 1/38; G01N 2001/386; G01N 2001/387; G01N 33/0027; G01N 33/0047;
(Continued)

(56) References Cited

U.S. PATENT DOCUMENTS

| | | | | |
|---|---|---|---|---|
| 7,828,947 | B2* | 11/2010 | Oki ..................... | G01N 33/6872 204/403.08 |
| 8,062,489 | B2* | 11/2011 | Oki .................. | G01N 33/48728 204/403.08 |
| 9,150,598 | B2* | 10/2015 | Schmidt .................... | C07F 9/22 |

FOREIGN PATENT DOCUMENTS

WO    WO 2011/043008 A1    4/2011

OTHER PUBLICATIONS

Barlow et al., "Rheological Droplet Interface Bilayers (rheo-DIBs): Probing the Unstirred Water Layer Effect on Membrane Permeability via Spinning Disk Induced Shear Stress", Scientific Reports vol. 7, 2017 (published online Dec. 14, 2017), pp. 1-12.
(Continued)

*Primary Examiner* — Justin N Olamit
(74) *Attorney, Agent, or Firm* — Birch, Stewart, Kolasch & Birch, LLP (57) ABSTRACT

The present invention provides a measuring device which includes: a first container and a second container that are arranged adjacent to each other; and a partition wall provided between the first and second containers, the partition wall having a through hole(s) for forming a lipid bilayer(s). In this measuring device, a gas flow path(s) having a hydrophobic surface is/are formed in at least one of the first and second containers; the gas flow path(s) has/have an inlet and an outlet; the inlet and the outlet each communicate with the exterior of the measuring device; the gas flow path(s) open(s) into the container in which it/they is/are formed; and a gas flowing in the gas flow path(s) contacts the droplet filled in the container.

4 Claims, 6 Drawing Sheets

(58) Field of Classification Search
CPC ....... G01N 33/48721; G01N 33/48728; G01N 33/5432
See application file for complete search history.

(56) References Cited

OTHER PUBLICATIONS

Fuji et al., "Pesticide vapor sensing using an aptamer, nanopore, and agarose gel on a chip", Lab Chip, vol. 17, 2017, pp. 2421-2425.
Misawa et al., "Highly sensitive and selective odorant sensor using living cells expressing insect olfactory receptors", PNAS, vol. 107, No. 35, Aug. 31, 2010, pp. 15340-15344.
Misawa et al., "Membrane protein-based biosensors", J.R. Soc. Interface, vol. 15 2018, pp. 1-17.
Sato et al., "Chemical Vapor Detection Using a Reconstituted Insect Olfactory Receptor Complex" Angew Chem Int. Ed., vol. 53, 2014, pp. 11798-11802.
Extended European Search Report for European Application No. 20872343.7, dated Sep. 5, 2023.
Nobukawa et al., "Electrical Detection of Pesticide Vapors by Biological Nanopores With DNA Aptamers", 2015, 28th IEEE International Conference on Micro Electro Mechanical Systems (MEMS), IEEE, Jan. 18-22, 2015, 596-599.

\* cited by examiner

MEASUREMENT INSTRUMENT AND METHOD FOR MEASURING TARGET SUBSTANCE USING SAME

TECHNICAL FIELD

The present invention relates to a measuring device that measures a target substance using a lipid bilayer, a method of measuring a target substance using the same, and a method of stirring a droplet filled in the measuring device.

BACKGROUND ART

Studies have been done for reconstituting olfactory receptors in lipid bilayers aiming to realize applications as sensors for odors and volatile organic compounds. Likewise, studies for sensors for odors and volatile organic compounds using cells and tissues have also been done in order to utilize a high sensitivity and specificity of living bodies.

However, since many of volatile organic compounds (target substances) are poorly soluble in water, to invent a mechanism for delivering a target substance to a receptor or cell capable of maintaining its activity only in an aqueous solution is required. Many studies have employed techniques in which a specified amount of target substance is dissolved in water to prepare a sample, and the sample is mixed with an aqueous solution infiltrating a receptor or cell (Non-patent Literature 1). Alternatively, there are examples in which agarose gel is used, as a method of passively taking in a target substance (Patent Literature 1 and Non-patent Literatures 2 to 4).

CITATION LIST

Patent Literature

Patent Literature 1: JP 2017-083210 A

Non-Patent Literature

Non-patent Literature 1: Nobuo Misawa et al., Proceedings of the National Academy of Sciences, 107, 15340, 2010.
Non-patent Literature 2: Satoshi Fujii et al., Lab on a Chip, 17, 2421, 2017.
Non-patent Literature 3: Nobuo Misawa et al., ACS sensors, 4, 711, 2018.
Non-patent Literature 4: Koji Sato et al., Angewandte Chemie International Edition, 53, 11798, 2014.

SUMMARY OF INVENTION

Problem to be Solved by the Invention

In cases where a target substance such as an odor or a volatile organic compound is dissolved into an aqueous solution which is a constituent of a sensor utilizing a receptor or the like, from a gas phase, issues to be addressed are poor solubility of the target substance (or a low distribution coefficient between gas and liquid) and a low diffusion coefficient of the target substance in the solution. Since the diffusion coefficient in the solution is about $10^{-9}$ m$^2$/s, a long period of time is required until the entire aqueous solution reaches vapor-liquid equilibrium. Therefore, it is thought that the time required for the target substance to be delivered to the receptor or the like which is a sensor element, in a sufficient concentration is also increased, resulting in an increase in the detection time (or a decrease in the sensitivity). As described above, while examples have been reported so far in which volatile molecules are detected by an artificial cell membrane sensor utilizing agarose gel, it has been difficult to detect dynamic changes in the concentration, since the target substance that has once dissolved in an aqueous solution is retained therein.

An object of the present invention is to provide: a measuring device in which a target substance can be efficiently introduced into a droplet, in a measurement using a lipid bilayer; a method of measuring a target substance using the same; and a method of stirring a droplet to be filled in the measuring device.

Means for Solving the Problem

As a result of intensive studies, the present inventors have discovered that, in the measurement of a target substance using a lipid bilayer, it is possible to efficiently introduce the target substance into a droplet in a container, by forming a gas flow path(s) having a hydrophobic surface, in contact with the container, and by flowing a gaseous sample containing the target substance through the gas flow path(s), thereby completing the present invention.

That is, the present invention provides the following:
(1) A measuring device comprising:
  a first container and a second container that are arranged adjacent to each other; and
  a partition wall provided between the first and second containers, the partition wall having a through hole(s) for forming a lipid bilayer(s);
  wherein
  a gas flow path(s) having a hydrophobic surface is/are formed in at least one of the first and second containers;
  each of the gas flow path(s) has an inlet and an outlet;
  the inlet and the outlet each communicate with the exterior of the measuring device;
  the gas flow path(s) open(s) into the container in which it/they is/are formed; and
  a gas flowing in the gas flow path(s) contacts the droplet filled in the container.
(2) The measuring device according to (1), wherein a plurality of the gas flow paths is formed.
(3) The measuring device according to (1) or (2), wherein the gas flow path(s) is/are in the form of a groove(s).
(4) The measuring device according to any one of (1) to (3), wherein the gas flow path(s) is/are provided at the bottom surface of at least one of the first and second containers.
(5) The measuring device according to any one of (1) to (4), wherein the first and second containers are in the form of a double-well chamber provided in a substrate.
(6) A measuring device comprising a plurality of units each composed of the measuring device according to any one of (1) to (5), wherein the inlets of the respective gas flow paths of the respective units communicate with each other through respective gas introduction paths, and a gas can be supplied simultaneously to the respective units during use.
(7) A method of measuring a target substance using the measuring device according to any one of (1) to (6), the method comprising the steps of:
  filling the first and second containers with droplets to form the lipid bilayer(s) in the through hole(s), and
  performing a measurement while flowing a gaseous sample containing the target substance through the gas flow path(s).

(8) The method of measuring a target substance according to (7), further comprising the step of removing the target substance in the droplet(s) by flowing a gas which does not contain the target substance through the gas flow path(s).

(9) A method of stirring a droplet in a measurement using a lipid bilayer, wherein, in the measurement of a target substance using the measuring device according to any one of (1) to (6), the method comprises the steps of: filling the first and second containers with droplets to form the lipid bilayer(s) in the through hole(s); and stirring the droplet(s) contacting the gas flow path(s) by flowing a gas through the gas flow path(s).

Effects of Invention

By performing a measurement using the measuring device according to the present invention, a target substance can be efficiently diffused into a droplet(s). Further, the target substance in the droplet(s) can be removed by flowing a gas which does not contain the target substance through the gas flow path(s). It is also possible to detect dynamic changes in the concentration of the target substance in a sample, by adding a new sample containing the target substance again after removing the target substance. In addition, it is also possible to stir the droplet(s) contacting the gas flow path(s) by flowing a gas through the gas flow path(s). As will be specifically shown in the Examples below, the signal detection efficiency is drastically increased by stirring the droplet(s).

DESCRIPTION OF EMBODIMENTS

Preferred embodiments of the present invention will now be described with reference to drawings. The drawings illustrating the measuring device are schematic diagrams for explaining the invention, and the dimension ratio of each portion is different from that of the actual measuring device.

Figure 1A:
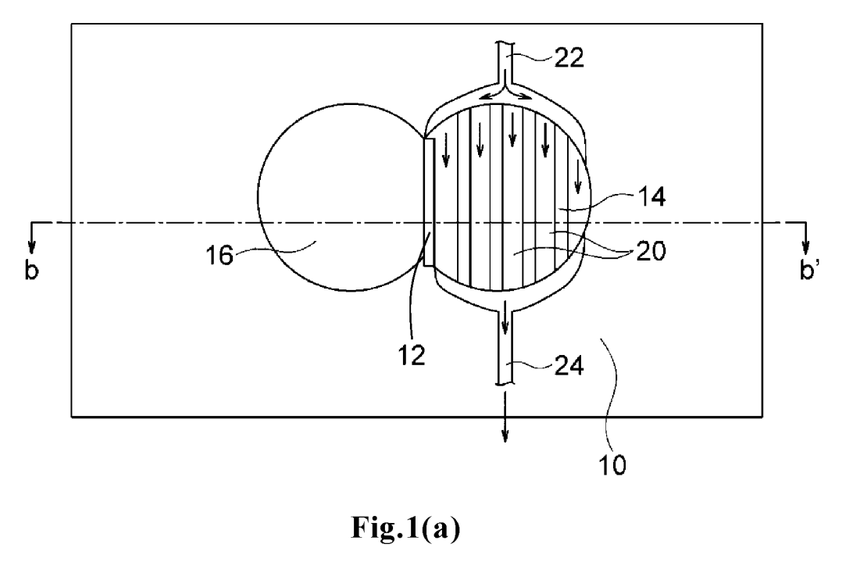
FIG. 1(a) is a schematic plan view of the measuring device according to the present invention.
Figure 1B:
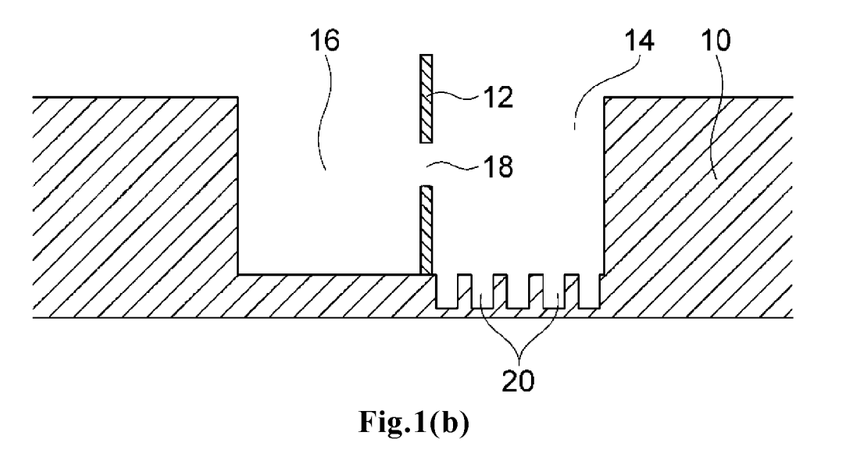
FIG. 1(b) is a cross-sectional end view taken along the line b-b' of the measuring device shown in FIG. 1(a).

FIG. 1(a) is a schematic plan view of the measuring device according to one preferred embodiment of the present invention, which is in the form of a double-well chamber (DWC), and FIG. 1(b) is a cross-sectional end view taken along the line b-b' of the measuring device shown in FIG. 1(a). The DWC is a structure in which two wells are arranged adjacent to each other in a substrate. The DWC is well known as a measuring device that uses a lipid bilayer, and also disclosed in Patent Literature 1 and the like. The device shown in FIG. 1 comprises: a substrate 10; a first well 14 which is the first container provided in the substrate 10; a second well 16 which is the second container provided in the substrate 10 and is adjacent to the well 14; and a partition wall 12 which is provided between the well 14 and the well 16, and which partitions these wells. The partition wall 12 is provided with a through hole(s) 18 for forming a lipid bilayer(s) at the time of using the device (see FIG. 1(b)). A plurality of gas flow paths 20 in the form of grooves are formed on the bottom surface of the well 14. The number of the gas flow paths 20 may be one, but a plurality of the gas flow paths 20 are preferably formed, because it enables to increase the contact between a gas and a droplet. The number of the gas flow paths 20 is preferably from about one to 50, but not particularly limited thereto. The gas flow paths 20 usually have a width of from about 0.001 mm to 2 mm, preferably from about 0.01 mm to 0.5 mm, and usually have a depth of from about 0.01 mm to 2 mm, preferably from about 0.2 mm to 0.8 mm. Each gas flow path 20 has an inlet and an outlet, and a gas flow enters from the inlet and exits from the outlet, during use. Each inlet communicates with a gas introduction path 22, and each outlet communicates with a gas discharge path 24. As shown by the arrows in FIG. 1(a), the gas introduced from the gas introduction path 22 during use enters from the inlets of the respective gas flow paths into the respective gas flow paths 20 and is discharged from the outlets of the respective gas flow paths 20 into the gas discharge path 24. Each well in the DWC can have the same size as that in a conventional DWC, and usually has a diameter of from about 1 mm to 10 mm, preferably from about 2 mm to 6 mm, and usually has a depth of from about 1 mm to 10 mm, preferably from about 2 mm to 6 mm. The through hole(s) 18 in the partition wall 12 has/have the same size as that in a conventional DWC, and usually has a diameter of from about 0.5 µm to 1,000 µm, preferably from about 10 µm to 600 µm.

At least the surface of each gas flow path 20 is hydrophobic. The hydrophobicity of the surface prevents the gas flow paths 20 from being blocked with liquid even when the well 14 is filled with a droplet, and enables to maintain spaces through which a gas can flow. The hydrophobicity can be easily imparted by performing a hydrophobic treatment on the gas flow paths 20. The hydrophobic treatment can be performed, for example, by coating a fluorine coating agent.

The DWC shown in FIG. 1 can be produced by: sticking an upper substrate that constitutes the side surfaces of the respective wells 14 and 16, to a lower substrate in which the gas flow paths 20, the gas introduction path 22 and the gas discharge path 24 have been formed by machining; and inserting and installing the partition wall 12 between the respective wells 14 and 16. The insertion of the partition wall 12 can be carried out by forming a groove or holes (42 in FIG. 4) into which the partition wall 12 is inserted, at the adjoining portion between the first well 14 and the second well 16, in advance, and inserting the partition wall 12 to the groove or holes. As is known, the partition wall 12 is preferably made of a parylene film or the like, in which a small through hole(s) can be easily formed.

The gas flow paths 20 can be easily formed by machining grooves on the bottom surface of the well 14, but is not limited to this method. The gas flow paths 20 can also be formed, for example, by arranging a fibrous, porous, plate-like or column-like member on the bottom surface. Further, the gas flow paths 20 need not be formed on the bottom surface, and may be formed on the side surface of the well. It is also possible to cover the top portion of the well with a lid, and to form the gas flow paths 20 on the under surface of the lid. However, it is easy to form the gas flow paths 20 on the bottom surface by machining, which is preferred. Although the gas flow paths are formed only in the first well 14 in the embodiment described above, they may also be formed in the second well 16.

As is well known, a through hole (38 or 40 in FIG. 3) for connecting an electrode is formed in each well, and each electrode contacts the droplet to be filled in each well, during use. A circuit that applies a predetermined voltage between both wells, and amplifies the flowing current to perform a measurement is connected to each electrode. Such a circuit is well known, and also described specifically in the Examples below (see FIG. 2(b)).

In operation, a lipid bilayer(s) is/are formed in the through hole(s) 18 in the partition wall 12 by the well-known droplet contact method. The method of forming a lipid bilayer is well known, and is also disclosed in Patent Literature 1. When a receptor protein or the like that should be reconstituted in the lipid bilayer(s) is added to a liquid to be filled into one of the wells, the protein is naturally reconstituted (retained) in the lipid bilayer(s). Examples of the protein include: various types of receptor proteins; peptide proteins such as α-hemolysin, gramicidin and alamethicin; various types of ion channels; and ABC transporter proteins; but not limited thereto.

After the formation of the lipid bilayer(s), a sample gas containing a target substance is introduced from the gas introduction path 22. The sample gas can be introduced into the gas introduction path 22, using a pump, a syringe or the like. This causes the sample gas to flow through each gas flow path 20, and to be discharged from the gas discharge path 24. At this time, the target substance in the sample gas flowing through each gas flow path 20 diffuses into the droplet filled in the well 14. By measuring the current flowing between both wells in this state, the target substance in the sample gas can be detected. The amount of gas to be introduced into the gas flow paths 20 is not particularly limited, and can be selected as appropriate. However, the amount of gas is usually from 0.001 L/min to 3 L/min, and preferably from 0.05 L/min to 1 L/min, in terms of the flow rate of the gas to be introduced into the gas introduction paths 20.

As will be specifically described in the Examples below, the diffusion rate of the target substance that diffuses from the gas flow paths 20 into the droplet is much higher than natural diffusion in a conventional method. Therefore, this enables to efficiently perform the measurement. Further, as has been revealed by the Examples below, the target substance contained in the droplet can be removed at least partially, by flowing a gas which does not contain the target substance, such as nitrogen gas which is an inert gas, through the gas flow paths 20. By flowing the sample gas containing the target substance again after at least partially removing the target substance as described above, it is also possible to continuously measure the changes over time in the concentration of the target substance in the sample gas.

In addition, as will be specifically described in the Examples below, it has been revealed that the droplet contacting the gas flow paths 20 is stirred, by flowing a gas through the gas flow paths 20. Conventionally, no method is known for stirring a small droplet in a measurement using a lipid bilayer. Therefore, the present invention also provides a method of stirring a droplet in a measurement using a lipid bilayer, wherein, in the measurement of a target substance using the measuring device according to the present invention described above, the method comprises the steps of: filling the first and second containers with droplets to form the lipid bilayer(s) in the measuring device; and stirring the droplet(s) contacting the gas flow path(s) by flowing a gas through the gas flow path(s). As will be specifically described in the Examples below, the signal detection efficiency is drastically increased by stirring the droplets, and therefore, stirring by gas introduction drastically improves the efficiency of the measurement using a lipid bilayer.

Figure 2A:
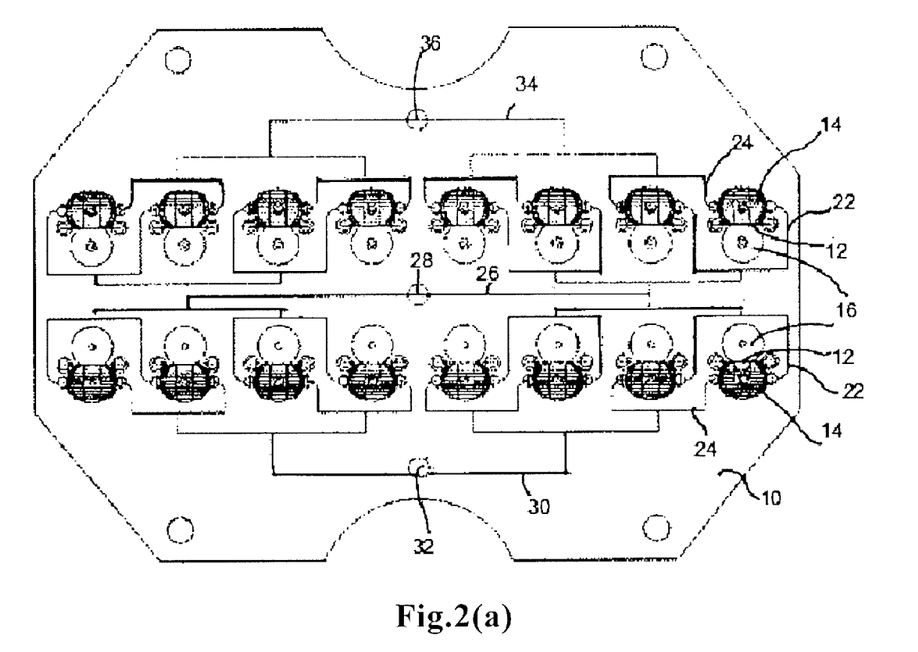
FIG. 2(a) is a schematic plan view of one specific example of the measuring device according to the present invention produced in the Examples below.

While one DWC is formed in the substrate 10 in the above-described embodiment, it is also possible to form a plurality of DWCs in a single substrate, merge the respective gas introduction paths 22 of the DWCs into one flow path, and perform measurements simultaneously by flowing the same gas simultaneously to the respective DWCs (see the Examples below and FIG. 4). In this case, by introducing a gas into a gas introduction main path (26 in FIG. 2) which is a major path where the respective gas introduction paths merge, the gas is introduced into the gas introduction paths 22 of the respective DWCs, and is discharged from the gas discharge paths 24 thereof through the respective gas flow paths 20. The respective gas discharge paths 24 merge into gas discharge main paths (30 and 34 in FIG. 2), and the gas is discharged from the substrate 10 therethrough.

In this manner, it is possible to improve the efficiency for detecting a target substance and to shorten the time required for detection operations, by connecting a plurality of units each comprising the first container, the second container and the partition wall to perform measurements simultaneously.

The present invention will now be specifically described with reference to Examples. It is noted, however, that the present invention is in no way limited to the following Examples.

Example 1

1. Production of Measuring Device

A measuring device in which 16 DWCs, each of which is one described above referring to FIG. 1, were formed in the substrate 10 was produced (FIG. 2). Each DWC includes the first well 14, the second well 16 and the partition wall 12, as described above. The above-described gas flow paths in the form of grooves are formed on the bottom surface of the first well 14 of each DWC. The respective gas introduction paths 22 merge into the gas introduction main path 26, and the gas introduction main path 26 communicates with a gas introduction hole 28. On the other hand, the respective gas discharge paths 24 connected to 8 DWCs located in the lower half of FIG. 2 merge into the gas discharge main path 30, and communicates with a gas discharge hole 32. In the same manner, the respective gas discharge paths 24 connected to 8 DWCs located in the upper half of FIG. 2 merge into the gas discharge main path 34, and communicates with a gas discharge hole 36.

Figure 3:
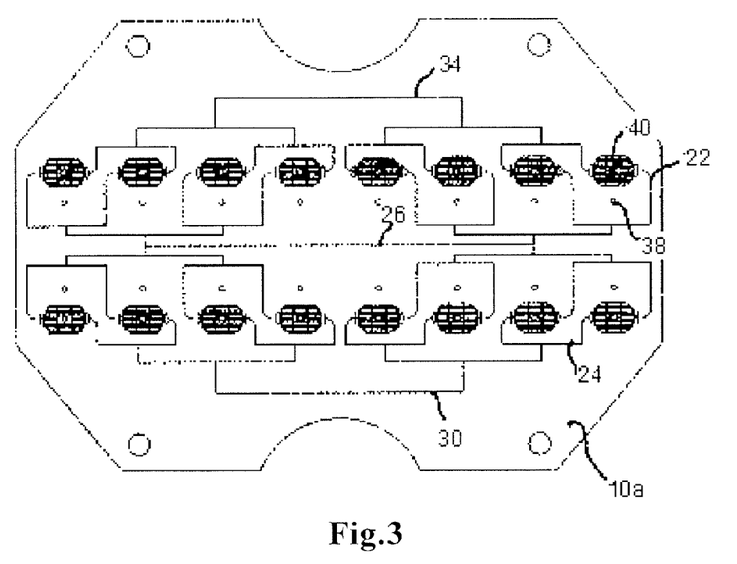
FIG. 3 is a schematic plan view of a lower substrate used in the production of the measuring device shown in FIG. 2.

The measuring device shown in FIG. 2 was produced as follows. As shown in FIG. 3, a lower substrate 10a composed of an acrylic plate having a thickness of 1 mm was provided, first. A plurality of gas flow paths in the form of grooves were formed in parallel to each other by machining, in the region that will constitute the bottom surface of the first well 14 of each DWC. The gas flow paths were machined using a mill having a diameter of 0.2 mm, and formed to a depth of 0.5 mm. The intervals between the respective gas flow paths in the form of grooves were set to 0.3 mm. Further, the gas flow paths in the form of grooves of each DWC were formed such that the paths have a length of from 3 mm to 8 mm and form an oval shape as a whole. In each DWC, the through holes 38 and 40 each for inserting an electrode and with a diameter of 0.56 mm were formed at the center of the region that will constitute the bottom surface of the first well 14 and at the center of the region that will constitute the bottom surface of the second well 16, respectively. Further, the gas introduction paths 22, the gas introduction main path 26, the gas discharge paths 24 and the gas discharge main paths 30 and 34 were machined in the shapes shown in FIG. 3. These gas flow paths were formed by machining using a mill having a diameter of 0.5 mm, and formed to a depth of 0.5 mm. Further, flow paths having a depth of 0.8 mm were machined at the inlet portions of the respective gas flow paths of each DWC, using a mill having a diameter of 1 mm, so that the inlets of the respective gas flow paths communicate with each other, and are connected to each corresponding gas introduction path 22. In the same manner, flow paths having a depth of 0.8 mm were machined at the outlet portions of the respective gas flow paths of each DWC, using a mill having a diameter of 1 mm, so that the outlets of the respective gas flow paths communicate with each other, and are connected to each corresponding gas discharge path 24.

Figure 4:
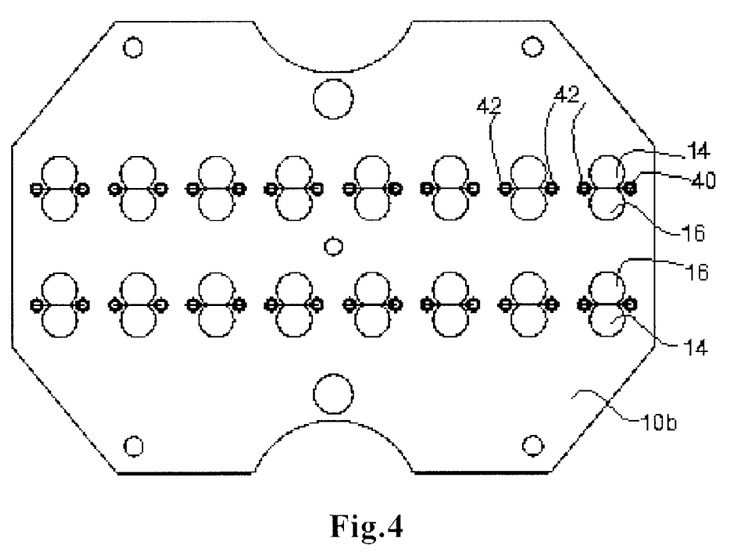
FIG. 4 is a schematic plan view of an upper substrate used in the production of the measuring device shown in FIG. 2.

On the other hand, as shown in FIG. 4, an upper substrate 10b composed of an acrylic plate having a thickness of 3 mm was provided. Through holes (diameter: 4.0 mm) that will form the respective wells, which are the first wells 14 and the second wells 16, were formed in the substrate by machining. Further, a pair of through holes 42 (diameter: 1.0 mm) for inserting each partition wall 12 were formed at the connecting portion of each pair of wells.

The lower substrate 10a shown in FIG. 3 and the upper substrate 10b shown in FIG. 4 were laminated and subjected to thermocompression bonding. In this state, each partition wall 12 composed of a parylene film was inserted to each pair of through holes 42. Each partition wall 12 is provided with eleven through holes for forming lipid bilayers and with a diameter of 100 μm. In this state, the gas flow paths in the form of grooves were hydrophobized by treating the bottom surfaces of the first wells with a hydrophobizing agent. SF-Coat SFE-B002H (manufactured by AGC Seimi Chemical Co., Ltd.) was used as the hydrophobizing agent, and the hydrophobic treatment was carried out by dropping from 3 to 6 μL of the hydrophobizing agent to the wells with grooves. The measuring device according to the present invention was prepared by the procedure described above.

Figure 2B:
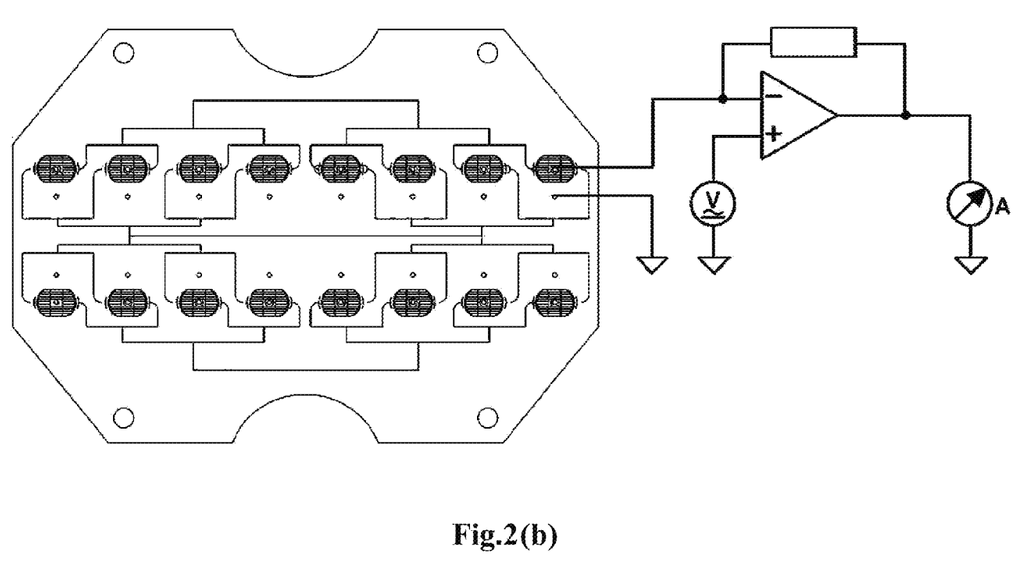
FIG. 2(b) is a view of the measuring device shown in FIG. 2(a) to which a circuit is connected.

Further, an electrode was inserted into each of the through holes 38 and 40 for inserting an electrode, each second well was grounded, and a voltage application and amplification circuit was connected to each first well. The voltage application and amplification circuit is shown in FIG. 2(b). Although the circuit is connected to only one DWC shown at the top right in FIG. 2(b) for simplicity, the same circuits were connected to all of the 16 DWCs, actually.

Example 2 Test for Confirming Whether or Not Gas is Uniformly Introduced into 16 DWCs To each of the second wells, 5 μL of a mixture of lipid DOPC (1,2-dioleoyl-sn-glycero-3-phosphocholine) and DOPE (1,2-dioleoyl-sn-glycero-3-phosphoethanolamine) (mass ratio 1:3, dissolved in n-decane at a concentration of 20 mg/ml) was added dropwise. Subsequently, 23 μL of Buffer 1 was added dropwise to each second well. The composition of Buffer 1 was as follows: NaCl (96 mM), KCl (2 mM), $MgCl_2$ (5 mM), $CaCl_2$ (0.8 mM), HEPES (5 mM)/pH 7.6. To each of the first wells, 28 μL of a 0.1 w/vol % aqueous solution of phenol phthalein was added dropwise. In this manner, lipid bilayers were formed in the through holes 18 in each partition wall 12.

On the other hand, a quantity of 1 mL of an ammonia solution (25%) was introduced into a vial and sealed. From the gas phase portion of the vial, 30 mL of ammonia gas was collected with a syringe. The collected 30 mL of ammonia gas was injected with the syringe into the gas introduction hole 28 (flow rate: about 0.5 ml/s) (see FIG. 2). Photographs were taken before the injection (0 second) of ammonia gas, and after the injection thereof every 5 seconds, until after 25 seconds. Phenolphthalein is an acid-base indicator, and turns reddish purple upon coming into contact with ammonia gas which is basic.

As a result, the colors of the solutions in the first wells turned reddish purple to the same degree in all of the 16 DWCs, and the reddish-purple color turned deeper over time. This confirmed that the ammonia gas injected from the gas introduction hole 28 was introduced uniformly to the first wells of all DWCs.

Example 3 and Comparative Example 1 Test for Confirming Improvement in Target Substance-Introduction Efficiency Due to Flowing of Gas Nitrogen gas was injected at a flow rate of 0.5 L/min, from the gas introduction hole 28 of the device produced in Example 1. To each of the second wells, 5 μL of the same lipid solution as that used in Example 2 was added dropwise, and 23 μL of the same Buffer 1 as that used in Example 2 was further added dropwise. To each of the first wells, 28 μL of Buffer 1 was added dropwise. In this manner, lipid bilayers were formed in the through holes 18 in each partition wall 12.

In this state, the injection of the nitrogen gas was stopped, and a gas with an octenol concentration of 5 ppm was injected from the gas introduction hole 28 at a flow rate of 0.5 L/min. A portion of the droplet in a first well was sampled, before the injection (0 minute) of the gas and after the injection thereof every 10 minutes, until after 30 minutes, and analyzed by gas chromatography to measure the octenol concentration.

In order to compare with the case where natural diffusion is simulated, the upper surface of the entire device was continuously exposed to a gas (flow rate: 0.5 L/min) with an octenol concentration of 15 ppm, without injecting the gas (Comparative Example 1). A portion of the droplet in a first well was sampled, before the exposure (0 minute) to the gas and after the exposure thereto every 10 minutes, until after 30 minutes, and analyzed by gas chromatography to measure the octenol concentration. The results are shown in FIG. 5.

Figure 5:
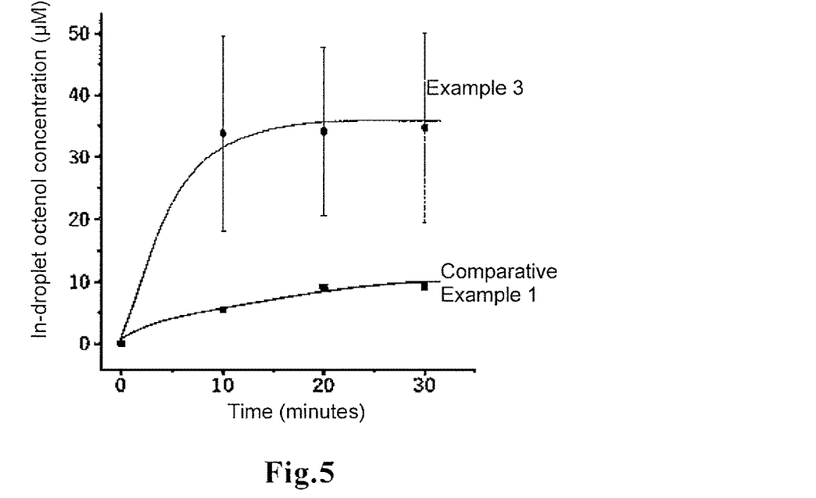
FIG. 5 is a graph illustrating a comparison of changes overtime in the octenol concentration in the droplet between the case where octenol gas was allowed to flow through the gas flow paths and the case where octenol gas was naturally diffused into the droplet, performed in Example and Comparative Example below.

As shown in FIG. 5, the octenol concentration in the droplet in the first well in Example 3 increased to 3 times or higher as compared to the case of Comparative Example 1, and in addition, nearly reached saturation 10 minutes after the start of the injection. It is noted here that such results were obtained regardless of the fact that the octenol concentration in Comparative Example 1 was 15 ppm, which is 3 times the octenol concentration (5 ppm) in Example 3 in which octenol was incorporated into the flowing gas. This confirmed that the target substance in the flowing gas diffuses into the droplet in the first well much more efficiently, as compared to the case of natural diffusion.

Example 4 and Comparative Example 2 Test for Confirming Improvement in Target Substance-Introduction Efficiency Due to Flowing of Gas and Formation of 16 Channels (Providing 16 DWCs)

Nitrogen gas was injected at a flow rate of 0.25 L/Min, from the gas introduction hole 28 of the device produced in Example 1. To each of the second wells, 5 µL of the same lipid solution as that used in Example 2 was added dropwise, and 23 µL of a solution obtained by mixing liposomes containing olfactory receptor protein to the same Buffer 1 as that used in Example 2 was further added dropwise. On the other hand, to each of the first wells, 28 µL of the same Buffer 1 as that used in Example 2 was added dropwise. In this manner, lipid bilayers were formed in the through holes 18 in each partition wall 12, and the olfactory receptor protein was reconstituted in the lipid bilayers.

An electrical measurement was started in this state. From the time point 10 minutes after the start of the measurement, octenol gas with a concentration of from 0.5 to 1 ppm was injected from the gas introduction hole 28. The octenol gas was injected at a flow rate of 0.25 L/min. When octenol is captured by the olfactory receptor protein, a current flows between the wells and is detected as a current signal. The time points at which signals were obtained were plotted chronologically, and the detection probability was estimated. In the "detection probability" as used herein, the population is taken as the number of measurements. (For example, in cases where four independent measurements were performed and signals were detected at the time points of 10 minutes, 20 minutes, 30 minutes and 40 minutes after the start of the measurement, the detection probability at the timepoint of 10 minutes is calculated as 1/4=25%, 20 minutes as 2/4=50%, 30 minutes as 3/4=75%, and 40 minutes as 4/4=100%.)

For comparison, a conventional measuring device in which one DWC was formed in a substrate was used, and the device was exposed to the octenol gas in the same manner as in Comparative Example 1, simulating natural diffusion. The results are shown in FIG. 6.

Figure 6:
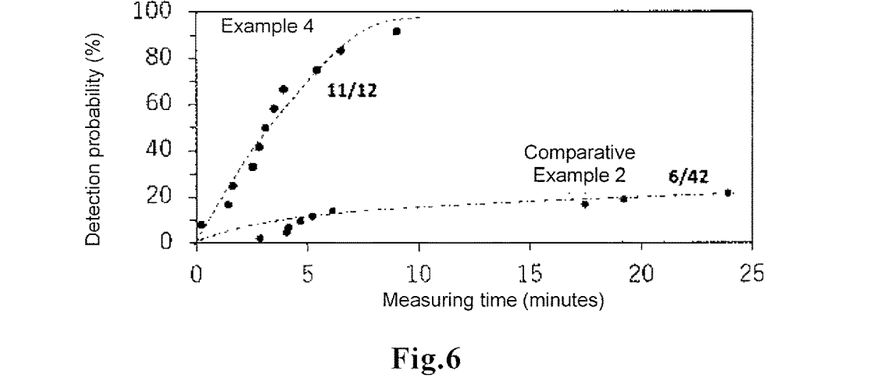
FIG. 6 is a graph illustrating the relationship between the measuring time and the signal detection probability, in the case where the 16-channel device according to the Examples of the present invention was used and the case where a conventional 1-channel device was used, obtained in Example and Comparative Example below.

As shown in FIG. 6, in the case of using the device of Example 1 in which the gas flows through the gas flow paths in 16 channels, the detection probability was much higher as compared to the case of using the conventional device with 1 channel and in which no gas flow path is formed.

Example 5 Continuous Dynamic Detection for About One Hour

Nitrogen gas was injected at a flow rate of 0.5 L/min, from the gas introduction hole 28 of the device produced in Example 1. To each of the second wells, 5 µL of the same lipid solution as that used in Example 2 was added dropwise, and 23 µL of a solution obtained by mixing liposomes containing olfactory receptor protein with the same Buffer 1 as that used in Example 2 was further added dropwise. To each of the first wells, 28 µL of Buffer 1 was added dropwise. In this manner, lipid bilayers were formed in the through holes 18 in each partition wall 12, and the olfactory receptor protein was reconstituted in the lipid bilayers.

Subsequently, an electrical measurement was started, while introducing 5 ppm octenol gas continuously generated by a gas generator, from the gas introduction hole 28. The octenol gas was switched to nitrogen gas at the time point 7 minutes after the start of the measurement, switched back to the octenol gas again at the time point of 25 minutes, and further switched again to the nitrogen gas at the time point of 50 minutes. Current signals indicating the opened state and closed state of olfactory receptor channels were obtained, and the opening rate (opened state/(opened state+closed state)) was estimated at each of the time points. On the other hand, in order to examine the octenol concentration in the droplet in the first well, the octenol concentration in the droplet was measured by gas chromatography under the same conditions. The results are shown in FIG. 7.

Figure 7:
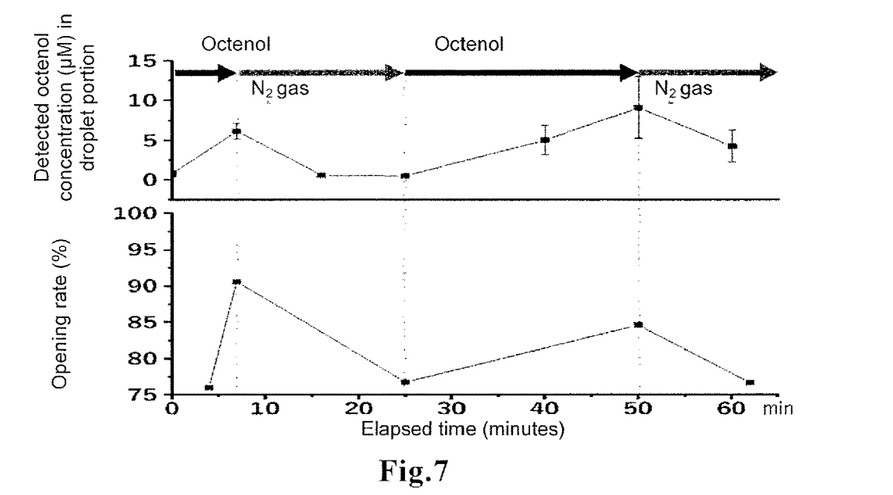
FIG. 7 is a graph illustrating the relationship between the time and the octenol concentration in the droplet or the opening rate of ion channels, when the gas to be introduced was switched from octenol gas to nitrogen gas, switched back to the octenol gas again, and further switched again to the nitrogen gas, obtained in Example below.

As shown in FIG. 7, it has been confirmed that when the flowing gas is octenol gas, the octenol concentration in the droplet increases and the opening rate also increases, whereas when the gas is switched to nitrogen gas, the octenol concentration in the droplet decreases to nearly 0, and the opening rate also decreases. That is, the above results confirmed that the target substance in the droplet can be removed from the droplet, by flowing a gas which does not contain the target substance.

Example 6 Stirring of Droplet Solution by Gas Introduction

To each of the second wells of the device produced in Example 1, 4.2 µL of a solution (20 mg/mL) of lipid DPhPC (1,2-diphytanoyl-sn-glycero-3-phosphorylcholine) in n-decane was added dropwise. Further, 21 µL of a solution (KCl 1M, phosphate buffer 10 mM pH 7.0) was added dropwise to each second well. To each of the first wells, 25 µL of a solution (KCl 1M, phosphate buffer 10 mM pH 7.0) containing microbeads (polystyrene beads, diameter: 75 µm) was added dropwise. In this manner, lipid bilayers were formed in the through holes 18 in each partition wall 12.

In this state, nitrogen gas was injected at a flow rate of 0.25 L/min from the gas introduction hole 28, and the movement of the microbeads before and after the injection of the gas was observed from the upper surface of the droplets.

As a result, the microbeads before the introduction of the nitrogen gas barely moved, but the microbeads started to move vigorously once the nitrogen gas was introduced. This has shown that that the solution constituting the droplets in the wells are stirred by gas introduction.

Example 7 Effect of Stirring Solution by Gas Introduction

Nitrogen gas was injected at a flow rate of 0.25 L/min, from the gas introduction hole 28 of the device produced in Example 1. To each of the second wells, 4.2 µL of a solution (20 mg/mL) of lipid DPhPC in n-decane was added dropwise. Further, 21 µL of a solution (KCl 1M, phosphate buffer 10 mM pH 7.0) containing 1 nM α-hemolysin was added dropwise to each second well. To each of the first wells, 25 µL of a buffer (KCl 1M, phosphate buffer 10 mM pH 7.0) containing 10 µM cyclodextrin was added dropwise. An electrical measurement was started, and after a while, nanopores derived from α-hemolysin were formed in the lipid bilayers, and blocking by cyclodextrin was started to be observed. After cyclodextrin-derived blocking signals were observed, the introduction of the nitrogen gas was stopped, and changes in the cyclodextrin-derived blocking signals were observed. The results are shown in FIG. 8.

Figure 8:
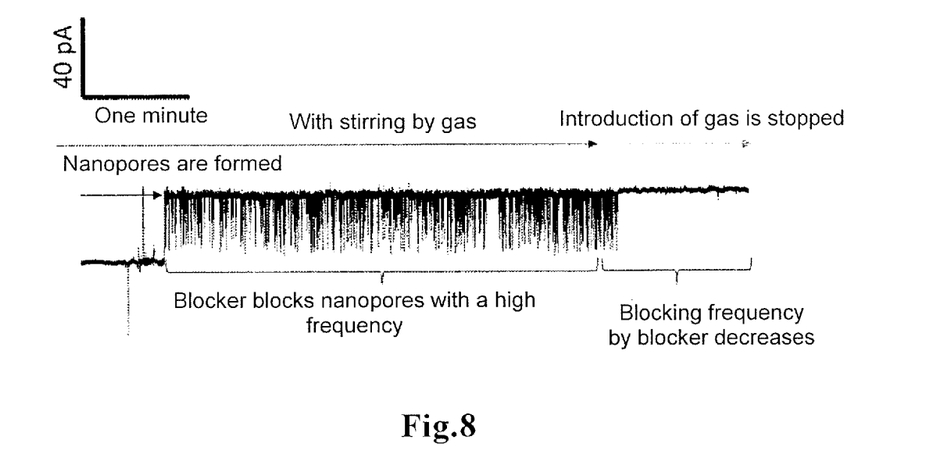
FIG. 8 is a diagram illustrating the results of the examination of the frequency at which cyclodextrin blocks the nanopores of α-hemolysin, when nitrogen gas was introduced and when the introduction of the gas was stopped, performed in Example below.

As shown in FIG. 8, when nitrogen gas is introduced, the α-hemolysin derived nanopores are blocked by cyclodextrin with a high frequency, whereas when the introduction of the nitrogen gas is stopped, the blocking frequency is drastically reduced. This confirmed that the signal detection efficiency is drastically increased by stirring the solution constituting the droplets.

DESCRIPTION OF SYMBOLS 10 substrate
12 partition wall
14 first well
16 second well
18 through hole
20 gas flow path
22 gas introduction path
24 gas discharge path
26 gas introduction main path
28 gas introduction hole
30 gas discharge main path
32 gas discharge hole
34 gas discharge main path
36 gas discharge hole
38 through hole for connecting an electrode
40 through hole for connecting an electrode
42 through hole for inserting partition wall 12

The invention claimed is:

1. A measuring device comprising a plurality of units each, comprising:
    a first container and a second container that are arranged adjacent to each other; and
    a partition wall provided between said first and second containers, said partition wall having one or more through hole(s) for forming one or more lipid bilayer(s);
    wherein
    one or more gas flow path(s) having a hydrophobic surface are formed in at least one of said first and second containers;
    each of said one or more gas flow path(s) has an inlet and an outlet;
    said inlet and said outlet each communicate with the exterior of said measuring device;
    said one or more gas flow path(s) open(s) into said at least one of the first and second containers in which they are formed; and
    a gas flowing in said one or more gas flow path(s) contacts the droplet filled in said at least one of the first and second containers, and wherein a plurality of the gas flow paths is formed;
    wherein the inlets of the respective gas flow paths of the respective units communicate with each other through respective gas introduction paths, and the gas can be supplied simultaneously to said respective units during use.

2. A method of stirring the droplet in a measurement using one or more lipid bilayers a lipid bilayer, wherein, in the measurement of a target substance using the measuring device according to claim 1, the method comprises the steps of:
    filling said first and second containers with droplets to form said one or more lipid bilayer(s) in said one or more through hole(s); and
    stirring the droplet(s) contacting the one or more gas flow path(s) by flowing a gas through said one or more gas flow path(s).

3. A method of measuring a target substance, the method comprising the steps of:
    providing a first container and a second container that are arranged adjacent to each other; and
    a partition wall provided between said first and second containers, said partition wall having a through hole(s) for forming a lipid bilayer(s);
    wherein
    a one or more gas flow path(s) having a hydrophobic surface is/are formed in at least one of said first and second containers;
    each of said gas flow path(s) has an inlet and an outlet;
    said inlet and said outlet each communicate with the exterior of said measuring device;
    said gas flow path(s) open(s) into the container in which it/they is/are formed; and
    a gas flowing in said gas flow path(s) contacts the droplet filled in said container;
    filling said first and second containers with droplets to form said one or more lipid bilayer(s) in said one or more through hole(s), and
    performing a measurement while flowing a gaseous sample containing said target substance through said one or more gas flow path(s).

4. The method of measuring a target substance according to claim 3, further comprising the step of removing said target substance in said droplet(s) by flowing a gas which does not contain said target substance through said one or more gas flow path(s).

* * * * *